United States Patent [19]

Drake et al.

[11] Patent Number: 4,727,213
[45] Date of Patent: Feb. 23, 1988

[54] POTASSIUM CARBONATE SUPPORTS, CATALYSTS AND PROCESSES THEREWITH

[75] Inventors: Charles A. Drake; Donald H. Kubicek, both of Bartlesville, Okla.

[73] Assignee: Phillips Petroleum Company, Bartlesville, Okla.

[21] Appl. No.: 3,177

[22] Filed: Jan. 8, 1987

Related U.S. Application Data

[62] Division of Ser. No. 811,985, Dec. 20, 1985, Pat. No. 4,661,466.

[51] Int. Cl.$^4$ ............................................. C07C 2/26
[52] U.S. Cl. .................................... 585/511; 585/516
[58] Field of Search ................................ 585/511, 516

[56] References Cited

U.S. PATENT DOCUMENTS

| | | | |
|---|---|---|---|
| 2,986,588 | 5/1961 | Schramm | 585/511 |
| 2,994,725 | 8/1961 | Shaw | 585/452 |
| 3,084,206 | 4/1963 | Yeo | 585/511 |
| 3,175,020 | 3/1965 | Wilkes | 585/516 |
| 3,175,021 | 3/1965 | Vanselow | 585/516 |
| 3,176,048 | 3/1965 | Yeo | 585/664 |
| 3,190,937 | 6/1965 | Yeo | 585/511 |
| 3,198,748 | 8/1965 | Keith | 502/74 |
| 3,207,812 | 9/1965 | Hambling | 585/511 |
| 3,260,770 | 7/1966 | Hambling | 585/329 |
| 3,297,779 | 1/1967 | Lodov | 585/510 |
| 3,305,599 | 2/1967 | Zadra | 585/511 |
| 3,325,559 | 6/1967 | Yeo | 585/511 |
| 3,331,884 | 7/1967 | Yeo | 585/511 |
| 3,340,323 | 9/1967 | Magerlein | 585/511 |
| 3,375,294 | 3/1968 | Beavers | 585/516 |
| 3,389,190 | 6/1968 | Alderson | 585/511 |
| 3,424,814 | 1/1969 | Hambling | 585/511 |
| 3,432,572 | 3/1969 | Taxema | 585/511 |
| 3,446,865 | 5/1969 | Roth | 585/250 |
| 3,755,491 | 8/1973 | Hashimoto | 585/511 |
| 3,756,963 | 9/1973 | Forni | 502/167 |
| 3,758,416 | 9/1973 | Forni | 502/184 |
| 3,816,298 | 6/1974 | Aldridge | 208/112 |
| 3,853,786 | 12/1974 | Forni | 502/174 |
| 3,916,019 | 10/1975 | Closson | 585/511 |
| 3,950,450 | 4/1976 | Hashimoto | 585/516 |
| 4,388,480 | 6/1983 | Imai | 585/516 |
| 4,520,126 | 5/1985 | Kawamoto et al. | 502/184 |
| 4,544,790 | 10/1985 | Drake | 585/516 |
| 4,656,154 | 4/1987 | Drake | 502/185 |

FOREIGN PATENT DOCUMENTS

| | | | |
|---|---|---|---|
| 83083 | 12/1982 | European Pat. Off. | 585/516 |
| 1553227 | 6/1975 | United Kingdom | 585/516 |

*Primary Examiner*—Curtis R. Davis
*Attorney, Agent, or Firm*—S. E. Reiter

[57] ABSTRACT

Catalyst supports, catalysts, method for the preparation thereof, and dimerization processes therewith are provided. Catalyst supports consist essentially of alkaline earth aluminate-containing potassium carbonate with at least one carbonaceous compound and having a crush strength of at least 5 pounds. Catalysts consist essentially of at least one elemental alkali metal deposited on the novel catalyst supports. Optionally, the catalysts further contain at least one promoter selected from the group consisting of elemental copper, elemental cobalt, and finely divided stainless steel.

15 Claims, No Drawings

POTASSIUM CARBONATE SUPPORTS, CATALYSTS AND PROCESSES THEREWITH

This application is a division of application Ser. No. 811,985, filed Dec. 20, 1985 now U.S. Pat. No. 4,661,466.

This invention relates to catalysts and catalyst supports. In one aspect, this invention relates to the preparation of catalysts. In another aspect, this invention relates to catalysts active for the dimerization of olefins. In yet another aspect, this invention relates to a process for the dimerization of olefins.

BACKGROUND

It is known in the art to employ supported alkali metal catalysts for such chemical conversions as propylene dimerization. In addition, the use of alkali metal carbonates as catalyst supports is known in the art. However, the use of such catalysts as alkali metals supported on alkali metal carbonate supports has been disadvantageous, especially in fixed bed operations, for the reason that the supports do not have sufficient strength to withstand the rigors of fixed bed operation. Instead, prior art olefin dimerization catalyst systems have frequently been limited to use in batch-type reaction due to the catalyst solubility or due to the fragile nature of the prior art particulate catalysts, i.e. the propensity of such catalysts to crumble under the conditions imposed by fixed bed operation.

Furthermore, prior art olefin dimerization catalysts do not always give high yields of the desired products, either due to low feed conversion, low product selectivity or both.

OBJECTS OF THE INVENTION

An object of this invention, therefore, is durable, particulate catalyst supports which are well suited for use in fixed bed operation.

Another object of the invention is durable, particulate catalysts for the dimerization of dimerizable olefins which are well suited for use in fixed bed operation.

Yet another object of this invention is a method for the preparation of the above mentioned catalysts.

Still another object of this invention is processes for the dimerization of dimerizable olefins.

These and other objects of the invention will become apparent from the disclosure and claims herein provided.

STATEMENT OF THE INVENTION

In accordance with the present invention, we have discovered that pelleting potassium carbonate in the presence of at least one alkaline earth aluminate, and a carbonaceous compound, and thereafter oxidatively removing a portion of the carbonaceous compound provides a rugged catalyst support with high initial crush strength as well as excellent long-term durability under chemical conversion conditions. The catalyst support prepared in accordance with our invention allows for the preparation of long-lasting, rugged (i.e., highly resistant to crumbling under chemical conversion conditions) elemental alkali metal dimerization catalysts having high dimerization activity.

DETAILED DESCRIPTION OF THE INVENTION

In accordance with the present invention, a method for producing a catalyst support is provided which comprises first pelletizing a mixture of potassium carbonate, in the range of about 1 up to 20 weight percent of at least one alkaline earth aluminate, and about 0.1 up to 10 weight percent of at least one carbonaceous compound, then heating the resulting pelletized product in an oxygen-containing atmosphere under conditions suitable to oxidatively remove in the range of about 10 up to 90% of the carbonaceous compound from the pelletized product. The resulting support is thereafter contacted, for example, with at least one elemental alkali metal in an oxygen-free atmosphere at a temperature sufficient to cause the alkali metal to melt, thereby producing a dimerization catalyst.

In accordance with another embodiment of the present invention, a support having a particle size of at least about 300 microns and a crush strength of at least about 5 pounds is provided consisting essentially of potassium carbonate, in the range of about 1 up to 20 weight percent of at least one alkaline earth aluminate, and about 0.09 up to 9 weight percent of at least one carbonaceous compound wherein the weight percentages are based on the total weight of potassium carbonate, alkaline earth aluminate and carbonaceous compound, and wherein the concentration of said carbonaceous compound is substantially less at the surface of said support than in the interior portions of said support. This differential content of carbonaceous compound between the support interior and exterior portions results from the partial oxidation of the support which is carried out after the potassium carbonate is pelletized. In a particular aspect of this embodiment, novel dimerization catalysts are provided consisting essentially of the above described alkaline earth aluminate-containing potassium carbonate support and about 0.1 to 20 weight percent of at least one alkali metal, wherein the weight percentages are based on the total weight of support and alkali metal.

In accordance with a further embodiment of the invention, an improved process is provided for the dimerization of dimerizable olefins with catalysts prepared as described hereinabove. Excellent feed conversions, product selectivities and long-term catalyst performance are obtained.

The alkaline earth aluminate-containing potassium carbonate support of the present invention is prepared by first pelletizing a mixture of potassium carbonate, in the range of about 1 up to 20 weight percent of at least one alkaline earth aluminate, and about 0.1 up to 10 weight percent of at least one carbonaceous compound, wherein the weight percentages are based on the total weight of potassium carbonate, alkaline earth aluminate and carbonaceous compound.

Potassium carbonate is readily available commercially and any such source is suitable. For purposes of this disclosure, the term alkaline earth aluminates is intended to include the various aluminates of Group IIA metals, such as, for example, magnesium aluminate, calcium aluminate and the like. For purposes of this disclosure, the term "carbonaceous compound" is intended to include various forms of the element carbon, including, but not limited to carbon black, charcoal, coconut charcoal, amorphous graphite, crystallite graphite, and the like, as well as mixtures of any two or more thereof. Finely divided graphite is presently preferred because it is useful both as a die lubricant for the pelleting process and it imparts dramatically improved activity to the finished dimerization catalyst.

The actual pelleting operation can be carried out in any suitable pelleting apparatus. If desired, lubricants such as stearic acid, rosin, hydrogenated coconut oil, and the like can also be added to the potassium carbonate-alkaline earth aluminate-carbonaceous compound mixture to be pelleted.

The pelleted support can then be subjected directly to the next step, i.e., the partial oxidation step, or, the support can optionally be ground into smaller size particles if desired for subsequent use.

The pelleted support, either as the pellets or as smaller crushed particles, is then heated in an oxygen-containing atmosphere under conditions suitable to oxidize in the range of about 10–90% of the carbonaceous compound. While suitable oxidation conditions can be readily determined by those of skill in the art, temperatures in the range of about 200° up to 900° C. for a time in the range of about 0.1 up to 48 hours are generally suitable. It is recognized by those of skill in the art that longer contact times will generally be appropriate at lower treatment temperatures and conversely, shorter contact times will be appropriate at higher treatment temperatures. Presently preferred treatment temperatures are in the range of about 250° up to 600° C. for a treatment time of about 0.5 up to 6 hours. Such treatment conditions will be expected to cause oxidation of at least 10% of the carbonaceous compound, but less than about 90% of the carbonaceous compound. Preferably, oxidative removal of about 20 up to 80% of the carbonaceous compound will be accomplished by this oxidation treatment; while most preferably, treatment conditions which cause the oxidation of about 30 to about 70% of the carbonaceous compound will be employed. As a result of this partial oxidation of the pelleted support, the concentration of carbonaceous compound remaining on the surface of the support is substantially less than the concentration of carbonaceous compound remaining in the interior portions of the support.

The pelleted support prepared as described hereinabove is very useful for the preparation of potassium carbonate supported catalysts because of the high initial crush strength of the resulting pellets or ground particulate material derived therefrom as well as excellent long-term durability under chemical conversion conditions. Thus, pellets prepared in accordance with the present invention have crush strengths of at least about 5 pounds. In most preparations, pellets having crush strengths of at least about 20 pounds are obtained, with crush strength as high as 50 pounds or higher possible. Due to the high crush strength of the alkaline earth aluminate-containing potassium carbonate supports prepared as described above, the pellets are useful in fixed bed operations directly as obtained from the pelleting process. Alternatively, the pellets can be crushed to smaller particle sizes if desired for more efficient packing of the particulate material in a fixed catalyst bed. For such purposes, the pelleted alkaline earth aluminate-containing potassium carbonate support of the invention retains its high crush strength for a particulate matter as small as about 300 microns. It is of course recognized by those of skill in the art that pellets of most any desired size can be prepared, e.g., ⅛ inch, 3/16 inch, ¼ inch, ⅜ inch, tc.

The pelleted, oxidized support is then subjected to treatment with at least one catalytically active material, or, if desired, it can optionally be ground into smaller size particles for subsequent use.

DIMERIZATION CATALYSTS

Dimerization catalysts employed in the practice of this invention consist essentially of the alkaline earth aluminate-containing potassium carbonate support prepared as described above, at least one elemental alkali metal and, optionally, one or more of the following promoters:

elemental copper,
elemental cobalt,
finely divided stainless steel, and mixtures of any two or more thereof. It should be recognized, however, that the catalysts of the invention can contain additional components which do not adversely affect the catalyst performance, such as, for example, pigments, dyes, processing aids, inert fillers, binders and the like.

The alkali metals contemplated to be within the scope of the invention include lithium, sodium, potassium, rubidium and cesium. While the proportion of elemental alkali metal combined with the alkaline earth aluminate-containing potassium carbonate support can vary appreciably, generally at least about one weight percent of elemental alkali metal, based on the total weight of treated support will be employed. Generally, in the range of about 1 up to 20 wt. % elemental alkali metal will be employed, with in the range of about 2 up to about 15 wt. % preferred. An elemental alkali metal loading in the range of about 3 up to 10 wt. % based on the total weight of treated support is most preferred for most efficient use of reagents, high catalyst activity and selectivity, ease of catalyst preparation and the like. Similarly, potassium is the preferred alkali metal due to its ready availability as well as ease and safety in handling.

The proportion of promoter, when employed, which can be combined with the alkaline earth aluminate-containing potassium carbonate support can vary appreciably, but generally, at least one weight percent of that promoter based on the total weight of treated support will be employed. The following amounts are provided for additional guidance:

|  | Loading, Wt. % | | |
| --- | --- | --- | --- |
| Promoter | Broad | Intermediate | Preferred |
| Cu | 1–30 | 3–20 | 5–12 |
| Co | 1–50 | 3–25 | 5–15 |
| SS* | 1–80 | 3–60 | 5–50 |

*Stainless steel

The general procedure for preparation of the dimerization catalysts of the invention involves contacting the pelletized support following the oxidation step with at least one elemental alkali metal in an oxygen-free atmosphere, such as, for example $N_2$, Ar or the like, at a temperature sufficient to cause the alkali metal to melt. The contacting is preferably carried out with vigorous stirring to ensure even distribution of the elemental alkali metal. Those of skill in the art recognize that suitable temperature for the contacting step will vary with the particular alkali metal employed. For example, with elemental potassium, temperatures in the range of about 80° C. to 100° C. are preferred, while with elemental sodium, temperatures in the range of about 100° C. to 140° C. are preferred.

While the alkali metal treated support is maintained at or above about 80° C., any desired promoter, such as for example, elemental copper, can be gradually added while the treated catalyst is continuously stirred. Catalyst is then ready to be charged to the reactor.

Optionally, the catalyst, once elemental alkali metal and any desired promoters have been deposited thereon, can be subjected to a subsequent heating step to ensure as uniform a distribution as possible of the various promoting metals on the surface of the alkaline earth aluminate-containing potassium carbonate support. Thus, the finished catalyst can be subjected to a temperature in the range of at least about 150° C. for a time in the range of about 0.1 up to 4 hours. A temperature in the range of about 250° up to 400° C. for a time in the range of about 0.5 up to 2 hours is presently preferred.

REACTANTS

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include "co-dimerization" as defined above.

Suitable dimerizable olefinic compounds are those compounds having from about 3 to about 30 caron atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as for example propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like, and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene, and the like, and mixtures of any two or more thereof.

The compounds indicated above are dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must, however, be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

REACTION CONDITIONS

The dimerization reaction of the invention can be carried out using either batch or continuous types of operation, although the catalysts of the invention are particularly well suited for continuous, i.e., fixed bed, operation. Suitable equipment, such as for example, autoclaves, tubular reactors, and the like, as are well known in the art, can be employed. No special materials of construction are required so that steel, stainless steel, glass-lined reactors, or the like can be employed.

The reaction temperature can vary depending on the catalyst and feed(s) employed. Typically, a temperature range of about 50° up to 250° C. is suitable. Temperatures in the range of about 80° up to 200° C. are preferred with a range of about 120° up to 160° C. most preferred because optimum reaction rates are obtained with minimum by-product formation.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures in the range of about 100 up to 5,000 psig are employed, with pressures in the range of about 1000 up to 4000 psig most preferred in order to achieve a good balance between raction rate while minimizing equipment and operating costs necessitated by very high reaction pressures.

If the reaction is carried out in the liquid phase, solvents or diluents for the reactants can be used. Saturated aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitrogen, argon, can be present.

The contact time required for the dimerization reaction depends upon several factors, such as for example, the activity of the catalyst, temperature, pressure, structure of the reactants employed, level of conversion desired, and the like. The length of time during which the dimerizable olefinic compounds are contacted with catalyst can vary conveniently in the range of about 0.1 seconds up to 24 hours although shorter and longer contact times can be employed. Preferably, times in the range of about one minute up to 5 hours are employed. Where reaction is carried out in continuous fashion, it is convenient to express the reactant/catalyst contact time in terms of weight hourly space velocity (WHSV), i.e., the ratio of the weight of reactant which comes in contact with a given weight of catalyst per unit time. Thus, a WHSV in the range of about 0.1 up to 10 will be employed. A WHSV is the range of about 0.5 up to 5 is preferred, with a WHSV in the range of about 1 up to 4 most preferred for optimum catalyst productivity.

PRODUCTS

The olefinic products of the invention have established utility in a wide variety of applications, such as for example, as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following non-limiting examples.

EXAMPLE I

Catalyst Preparation

Catalyst support was prepared by pelleting commercially available anhydrous potassium carbonate on a Stokes-Pennwalt Model 900-511-6 Eureka Tabletting Machine. Pellets (⅛") were prepared and used directly, or crushed and sieved to recover a desirable particle size. The potassium carbonate was admixed with varying amounts of an alkaline earth aluminate and various amounts of a carbonaceous compound prior to being subjected to the pelleting process.

After pelleting, the alkaline earth aluminate, carbonaceous compound-containing potassium carbonate pellets (or crushed, sieved material) were subjected to a "burnoff" period in an oxygen-containing atmosphere at a temperature of about 350°-900° C. for times in the range of about 0.5 up to 5 hours.

Following the burnoff treatment, the support was warmed to about 200° C. to 250° C., then allowed to cool to about 80°-85° C., a which time the desired alkali metal, and optionally finely divided stainless steel (designated as SS in Table I), were added. After the alkali metal and SS had been thoroughly contacted with the support, an optional post-treatment was carried out in an inert atmosphere. Thus, the finished catalyst was typically heated to about 200°-250° C. for about 0.25 up to 4 hours in order to ensure a fairly uniform distribution of alkali metal (and any other promoter) on the catalyst support.

The specific details on the preparation of catalysts used in Example II, e.g., die lubricant, burnoff conditions, post-treatment conditions, alkali metal and promoter levels, are summarized in Table I.

Several of the catalyst supports, before K treatment, were analyzed for residual carbon content after the burnoff period. Representative values are presented in Table II.

TABLE II

| Carbon Content of Pelleted Catalyst Support | | | |
|---|---|---|---|
| Burnoff | | Carbon Content, Wt % | |
| Temp, °C. | Time Hr. | Initial | Final |
| 350 | 1 | 1.0 | 0.8 |
| 350 | 3 | 1.0 | 0.7 |
| 350 | 5 | 1.0 | 0.2 |
| 450 | 3 | 1.0 | 0.3 |
| 600 | 3 | 1.0 | 0.1 |

The potassium carbonate pellets were visually inspected both before and after the "burnoff" step. Whereas unoxidized support was uniformly black throughout, the oxidized support was gray on the surface, while the interior portions remained black. Thus, even by visual inspection alone, it is clear that the concentrations of carbonaceous compound is less at the surface of the support compared to the concentration of carbonaceous compound in the interior portions of the support. However, upon severe oxidation treatment, such as for example, 900° C. for 30 minutes, the support evidences no residual carbon content by visual inspection.

The crush strengths of several pelleted potassium carbonate supports were determined employing a pellet strength tester instrument. The typical crush strength of a ⅛" diameter pellet was found to vary within the range of about 20–30 pounds. This is far superior to the crush strength of granular (about 6 mesh) potassium carbonate, which is only about 3 pounds.

EXAMPLE II

Dimerization of Propylene

Typically, the dimerization of propylene was carried out in a steam heated 316 stainless steel tubular reactor (⅜"×20"). The catalyst (50 g; density ~1.1 g/mL), bounded above and below by small volumes of glass beads, was heated to the reaction temperature of 150° C. at about 1500 psig and the propylene was pumped into the reactor at a rate of about 120 mL/hr. After about 6 hours of reaction time a sample was taken and analyzed by gas liquid chromatography (glc). After the 6 hours of reaction time, the catalyst was removed from the reactor and inspected to determine its physical condition after the 6 hours exposure to dimerization conditions. Results of numerous propylene dimerization reactions are summarized in Table III.

TABLE I

| | | | Catalyst Preparation | | | | | |
|---|---|---|---|---|---|---|---|---|
| Catalyst | Graphite, Wt. % | CaAl₂O₄, Wt. % | Burnoff Temp., °C. | Time, hours | Alkali Metal, Wt. % | Promoter, Wt. % | Post-Treatment Temp., °C. | Time, hours |
| A | 1.0 | None | 350 | 3 | K,4.5 | SS,4.5 | 250 | 1 |
| B | 1.0 | 2.4 | 350 | 3 | K,4.5 | SS,4.5 | 250 | 1 |
| C | 1.0 | None | 450 | 3 | K,4.5 | SS,4.5 | 250 | 1 |
| D | 1.0 | 4.7 | 450 | 3 | K,4.5 | SS,4.5 | 250 | 1 |
| E | 1.0 | None | 450 | 3 | K,4.5 | SS,4.5 | 250 | 1 |
| F | 1.0 | 2.4 | 450 | 3 | K,4.5 | SS,4.5 | 250 | 1 |

TABLE III

| Propylene Dimerization | | | |
|---|---|---|---|
| Run No. | Catalyst | Propylene Conv., % | Selectivity to 4-MP-1, % | Catalyst Condition |
| 1 | A | 18 | 90 | (1) |

TABLE III-continued

| Run No. | Catalyst | Propylene Dimerization | | Catalyst Condition |
| --- | --- | --- | --- | --- |
| | | Propylene Conv., % | Selectivity to 4-MP-1, % | |
| 2 | B | 13 | 89 | (2) |
| 3 | C | 16 | 85 | (1) |
| 4 | D | 15 | 78 | (2) |
| 5 | E | 16 | 85 | (1) |
| 6 | F | 11 | 82 | (2) |

(1) Catalyst particles had collapsed, i.e., they were reduced to a fine powder, rather than physically distinct pellets.
(2) Catalyst particles remained predominantly intact, i.e., pellets were essentially intact with only a small amount (less than 10 wt. % of original catalyst charge) of powdered fines being observed.

The results in Table III indicate that propylene conversion and selectivity to 4-methyl-1-pentene is comparable for control catalysts A, C and E (runs 1, 3 and 5) compared to invention catalysts B, D and F (runs 2, 4 and 6). The durability of the catalysts, however, is dramatically different, as noted in the last column of the table. Thus, control catalysts, A, C and E were reduced to a structureless powder, essentially unusable for further fixed bed reaction, after only 6 hours of reaction. Conversely, the invention catalysts B, D and F substantially retained their physical integrity when subjected to identical reaction conditions. The invention catalysts could, therefore, be used for fixed bed chemical conversion for far greater periods of time than could the control catalysts.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

I claim:

1. A process for the dimerization of at least one dimerizable olefin which comprises contacting at least one dimerizable olefin under dimerization conditions with a catalyst consisting essentially of:
   (i) a support consisting essentially of potassium carbonate,
   in the range of about 1 up to 20 weight percent of at least one alkaline earth aluminate,
   in the range of about 0.09 up to 9 weight percent of at least one carbonaceous material selected from the group consisting of:
   carbon black,
   charcoal,
   amorphous graphite, and
   crystallite graphite;
   wherein said weight percent ranges are based on the total weight of potassium carbonate, alkaline earth aluminate, and carbonaceous material and wherein the concentration of said carbonaceous material is substantially less at the surface of said support than in the interior portions thereof; and
   (ii) in the range of about 0.1 up to 20 weight percent of at least one elemental alkali metal deposited on the surface of said support; wherein said weight percent ranges are based on the total weight of support and elemental alkali metal.

2. A process in accordance with claim 1 wherein said contacting is carried out at a temperature in the range of about 50° up to 250° C., a pressure in the range of about 100 up to 10,000 psig, and a weight hourly space velocity in the range of about 0.1 up to 10.

3. A process in accordance with claim 1 wherein said at least one elemental alkali metal is elemental potassium.

4. A process in accordance with claim 1 wherein said at least one alkaline earth aluminate is calcium aluminate.

5. A process in accordance with claim 3 wherein said at least one alkaline earth aluminate is calcium aluminate.

6. A process in accordance with claim 1 wherein said at least one dimerizable olefin is propylene.

7. A process in accordance with claim 3 wherein said at least one dimerizable olefin is propylene.

8. A process in accordance with claim 5 wherein said at least one dimerizable olefin is propylene.

9. A process in accordance with claim 1 wherein said catalyst further contains at least one component selected from the group consisting of:
   elemental cobalt,
   elemental copper, and
   finely divided stainless steel.

10. A process in accordance with claim 3 wherein said catalyst further contains at least one component selected from the group consisting of:
    elemental cobalt,
    elemental copper, and
    finely divided stainless steel.

11. A process in accordance with claim 5 wherein said catalyst further contains at least one component selected from the group consisting of:
    elemental cobalt,
    elemental copper, and
    finely divided stainless steel.

12. A process in accordance with claim 8 wherein said catalyst further contains at least one component selected from the group consisting of:
    elemental cobalt,
    elemental copper, and
    finely divided stainless steel.

13. A process according to claim 1 wherein said carbonaceous material is coconut charcoal.

14. A process according to claim 8 wherein said carbonaceous material is coconut charcoal.

15. A process according to claim 12 wherein said carbonaceous material is coconut charcoal.

* * * * *